United States Patent [19]
Dam et al.

[11] Patent Number: 5,663,503
[45] Date of Patent: Sep. 2, 1997

[54] INVASIVE AND NON-INVASIVE ULTRASONIC SENSOR WITH CONTINUOUS AND DEMAND SELF-TEST

[75] Inventors: Naim Dam, Muttontown; Michael J. Marro, Plainview, both of N.Y.

[73] Assignee: Cosense, Inc., Hallppauge, N.Y.

[21] Appl. No.: 525,929

[22] Filed: Sep. 8, 1995

[51] Int. Cl.⁶ .................................................. G01N 29/02
[52] U.S. Cl. ........................................ 73/649; 73/1.82
[58] Field of Search ........................ 73/1 DV, 649, 73/661, 1 M, 290 V, 599, 600, 602, 610, 612; 367/13, 908; 324/76.49; 340/621

[56] References Cited

U.S. PATENT DOCUMENTS

| | | | |
|---|---|---|---|
| 4,630,245 | 12/1986 | Dam | 340/621 |
| 5,269,188 | 12/1993 | Esin | 73/610 |
| 5,437,178 | 8/1995 | Esin | 73/612 |
| 5,452,611 | 9/1995 | Jones | 73/1 DV |

*Primary Examiner*—Christine K. Oda

[57] ABSTRACT

An ultrasonic sensor of either the invasive or non-invasive type having a piezoelectric element for transmitting and receiving ultrasonic energy bonded by an adhesive to the inner face of the wall of a support. When operated in an energy transmitting mode, the energy transmitted by the element is reflected from the interface of the outer face of the wall medium confronting it back to the element. The distance from the front face of the element through the bonding adhesive to the interface is known and when the sensor is in a receiving mode the time of arrival of the reflected signal can be predicted. The received energy is used as a self-test signal to check element dis-bonding. In one embodiment sensor integrity is checked by a digital signal processing technique with the received signal reflected from the interface being periodically sampled and converted into a series of digital numbers. The digital numbers are processed by a cross-correlation technique with a signature signal corresponding to a properly operating sensor. If the element is dis-bonded there will either be no signal reflected from the interface or the reflected signal will not produce the proper series of number corresponding to a properly operating sensor. Detection of a dis-bonded element is accomplished for conditions of the gap being either wet or dry.

16 Claims, 5 Drawing Sheets

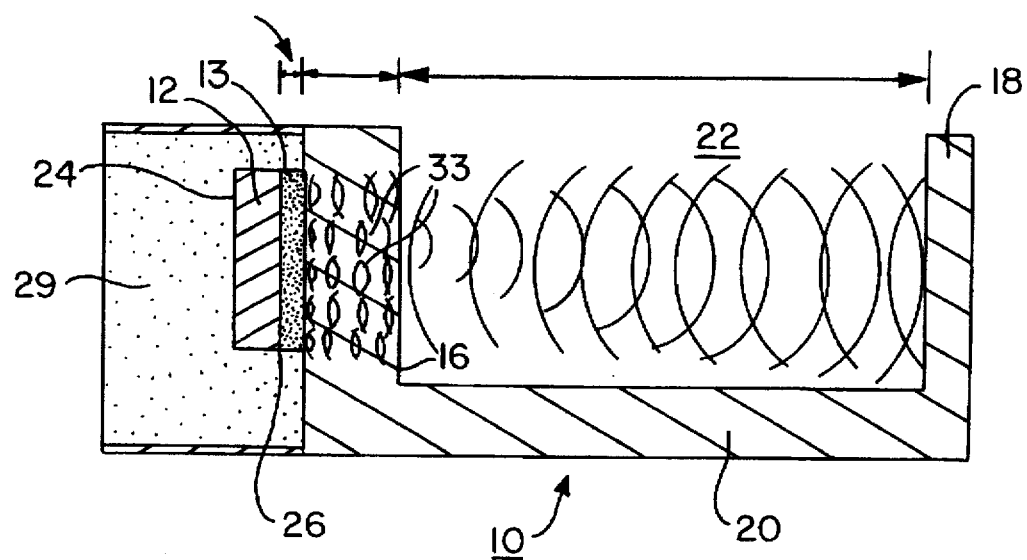
FIG. 1
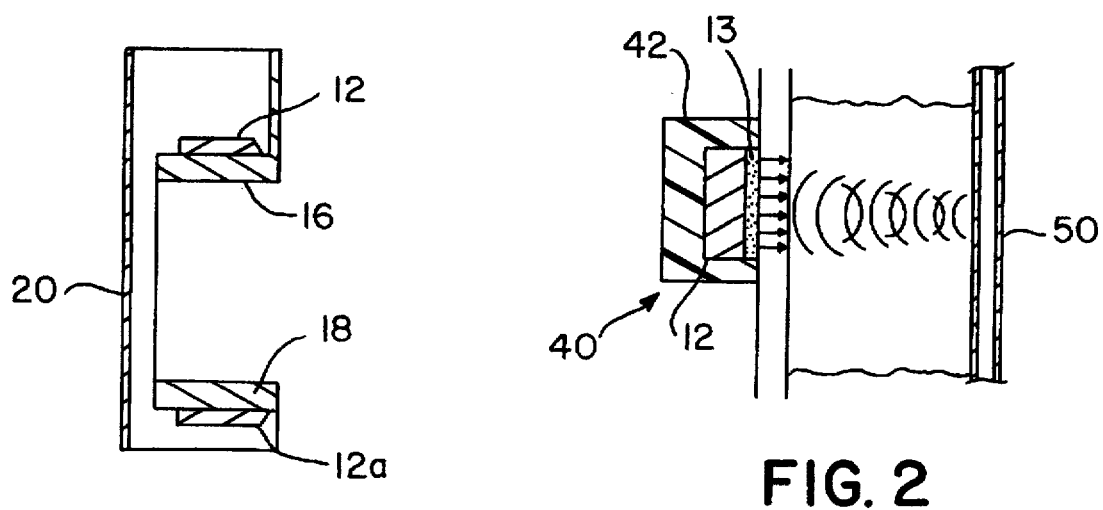
FIG. 1A
FIG. 2

INVASIVE AND NON-INVASIVE ULTRASONIC SENSOR WITH CONTINUOUS AND DEMAND SELF-TEST

FIELD OF THE INVENTION

The present invention relates to ultrasonic sensors and a system for the self-test of whether the piezoelectric transducer element used in the sensor is properly bonded to a sensor support face.

BACKGROUND OF THE INVENTION

Ultrasonic sensors used for measuring the presence of a liquid in a vessel are well known. One type is called a contact, or invasive, type sensor. This type of sensor utilizes a support structure defining a gap into which the liquid flows. In such sensors a piezoelectric (crystal) transducer element is bonded by a suitable adhesive, such as an epoxy, to the inner face of one or both surfaces of the structure forming the gap. The element transmits energy and if there is liquid present in the gap the energy will travel across the gap. If there is no liquid in the gap the energy will be attenuated in the air.

In an invasive sensor using one element, energy is transmitted through the liquid to the opposing surface of the gap structure from which it is reflected back to the element. Detection of the reflected signal indicates the presence of liquid in the gap. In a two element invasive type sensor, there is an element on the inner face of each surface of the gap defining structure. Here, the second element receives the energy transmitted through the liquid across the gap and indicates liquid presence. The same effect occurs when there is any other type of sound energy transmitting material in the gap.

Another well known sensor is the non-contact, or non-invasive, type in which the sensor is mounted externally of a pipe or vessel. In this type of sensor the liquid does not come into contact with the sensor. The transmitted energy from the element is travels through the wall of the pipe or vessel to which it is mounted and the liquid to be reflected from an opposing wall of the pipe or vessel to which the sensor is mounted and is reflected back to the element. If there is no liquid, the energy is attenuated in the interior of the pipe or vessel. In a properly operating sensor a portion of the energy is reflected back to the element from the interface of the interior of the wall of the pipe or vessel and its interior, whether wet or dry.

It is desired to provide such sensors with self-test capability to check, either continuously or on demand, failure of any of the sensor components. This includes the bonding of the piezoelectric element, or elements, to the respective inner face, or faces, of the gap surfaces. That is, it is desired to determine if an element has become dis-bonded. If an element has become dis-bonded, the sensor will always signal a 'dry' condition, that is, that there is no liquid in the gap. This indication will be given falsely even if the gap is 'wet', that is, there is liquid present. Dis-bonding of an element occurs for a variety of reasons such as dropping of the sensor, rapid temperature changes (thermal shock) and other factors. In effect, dis-bonding of an element causes the sensor to become inoperative. A similar situation occurs in non-contact type sensors.

One arrangement intended to check the integrity of a sensor is disclosed in U.S. Pat. No. 5,269,188 to Esin et al granted Dec. 14, 1993. This patent discloses a frame type sensor support structure in which a stem connects the two gap forming surfaces. In a sensor using two elements, one is bonded to the interior of one of the surfaces forming the gap and serves as a transmitter and the other is bonded to the other surface and serves as a receiver. When energy is transmitted from the transmitter element an amount passes, or leaks, directly through the stem part of the sensor support frame connecting the two surfaces forming the gap and is received by the receiver element for use as a self-test signal. This leaked energy does not travel across the gap and it is used as a self-test signal.

A period of time, or time window, for this self-test signal travelling through the support frame to be received by the element mounted to the other surface of the frame gap is set in relation to a time window at which the main energy passing through liquid in the gap, if present, is to be detected. The appearance of a signal in the self-test time window, which should occur both in wet and dry gap conditions, is to indicate that the sensor is supposed to be functioning properly. However, this arrangement is not fully capable of checking for dis-bonding of a piezoelectric element, or elements. This is due to the fact that energy can leak out from the back surface or sides of a dis-bonded element and travel through the stem to the receiver element. This situation is sometimes referred to as 'cross-talk'. Cross-talk also can occur in a sensor using only one element in that the part of the energy used for self-test can leak through the stem to the opposing surface for transmission through liquid in the gap back to the one element and give an indication of the sensor operating properly or not.

OBJECTS OF THE INVENTION

It is an object of the invention to provide for a sensor with capability of continuous or demand self-test of the integrity of an ultrasonic sensor relative to dis-bonding of its piezoelectric element, of elements, from a part of the sensor support structure.

Another object is to provide a self-testing ultrasonic sensor that checks either on demand or continuously the integrity of the bonding of the piezoelectric transducer element, or elements, to the sensor support structure by measuring the distance, which is known, from the element through the bonding adhesive to the wall of the support structure to which the element is mounted.

Yet another object is to provide an ultrasonic sensor with self-test capability in which signals transmitted and received by the sensor are mapped over a plurality of cycles and compared to determine if there is a reflection from the wall of the sensor to which an element is bonded.

A further object is to provide an ultrasonic sensor in which a signal is transmitted from a piezoelectric element through the adhesive bonding the element to a sensor support wall and is reflected from the interface at the wall and the reflected signal is detected to determine that the element is properly bonded to the sensor support.

Yet another object is to provide a sensor in which there is a self-test of element dis-bonding that operates continuously or on demand for both wet and dry conditions of the sensor gap.

BRIEF DESCRIPTION OF THE INVENTION

In accordance with the invention an ultrasonic sensor of either the invasive or non-invasive type has a piezoelectric element for transmitting and receiving ultrasonic energy bonded by an adhesive to a support surface. When operated in an energy transmitting mode, the energy transmitted by the element is reflected from the interface of the wall supporting the element, or the interior of the pipe or vessel in the case of a non-invasive sensor, and the medium it confronts back to the element. The distance from the front face of the element through the bonding adhesive to the interface is known. Therefore, when the sensor is in a receiving mode the time of arrival of the reflected signal can be predicted. The received energy is used as a self-test signal to check element dis-bonding.

In a preferred embodiment of the invention sensor integrity is checked by a digital signal processing technique. That is, the received signal reflected from the interface is periodically sampled and converted to a series of digital numbers. The digital numbers are processed by a cross-correlation technique with a digital signature signal corresponding to a properly operating sensor. If the element is totally dis-bonded or partially dis-bonded there will either be no signal reflected from the interface or the reflected signal will not produce the proper series of numbers corresponding to the signature of a properly operating sensor. Detection of a dis-bonded element is accomplished for conditions of the gap being either wet or dry.

The digital signal processing technique also can be used to determine various characteristics of the liquid in and through which the ultrasonic energy signal is transmitted.

In another embodiment of the invention a window is set to detect reception of the energy reflected from the interface of the support wall and the gap. The timing of the window can be set since the round trip time of the energy transmitted from the element and the interface is known with a fair degree of precision. In a properly operating sensor in which the element is not dis-bonded, the reflected signal will be received at the time of occurrence of the window.

BRIEF DESCRIPTION OF THE DRAWINGS

Other objects and advantages of the present invention will become more apparent upon reference to the following specification and annexed drawings in which:

FIG. 1 is a cross-sectional view of a typical sensor showing mounting of its components;

FIG. 1A is a cross-sectional view of a sensor using two piezoelectric elements;

FIG. 2 is a cross-sectional view of a non-contacting type sensor;

DETAILED DESCRIPTION OF THE INVENTION

Figure 3:
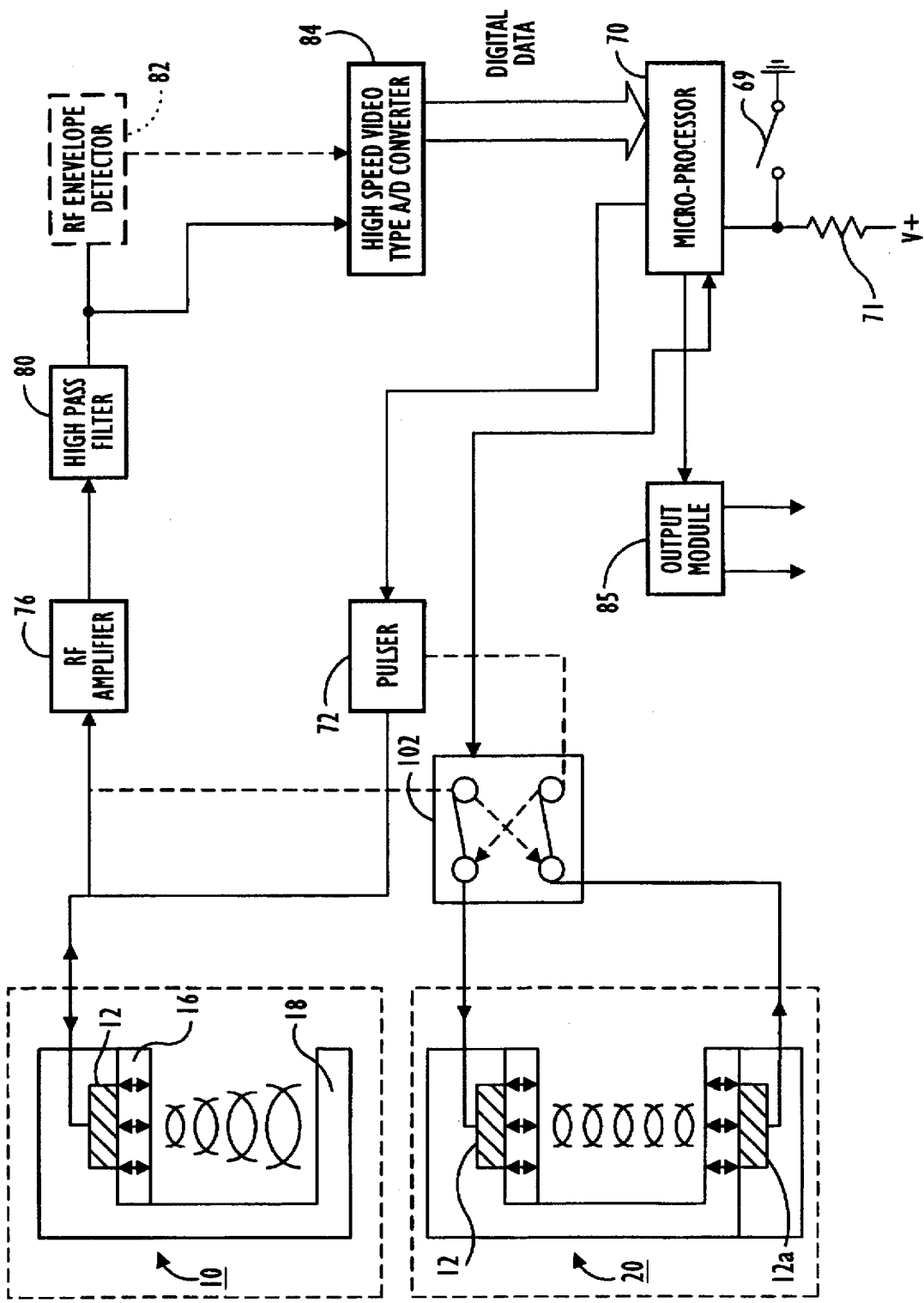
FIG. 3 is a schematic block diagram of a first embodiment of a circuit for a sensor with continuous or demand self-test capability.

FIG. 1 show details of a gap type sensor 10 having a single piezoelectric crystal transducer element 12. The sensor includes a support structure having a first end 16 of thickness 't' and a second end 18 joined by a stem 20 defining a gap 22 of distance 'l' between the inner faces of the support ends 16, 18. The element 12 is a relatively thin disk of piezoelectric material, such as PZT and preferably of PVDE type, a flexible plastic material made by AMP of Harrisburg, Pa., and can be of circular or rectangular shape. The sensor support ends 16, 18 can be of any desired shape, such as circular, and the connecting stem 20 of arcuate, circular or other suitable shape.

An electrode (not shown) is plated on each face of the element 12 and a lead wire (also not shown) is connected to each electrode to provide connection between the element and a source of exciting energy and/or to receiving circuits, as described below. The thickness of the element is generally about one-half wavelength of the sensor operating frequency.

In a typical sensor, one face 13 of the element, the one to be bonded to the support, is covered with a coating of an abrasion resistant material, such as epoxy, of a thickness of approximately one-fourth wavelength of the operating frequency. The other element face is covered with one or more layers of a backing material 24, such as epoxy, to absorb acoustic energy produced by the element when excited to prevent this energy from returning via the rest of the support structure to the element. The face 13 of the element with the abrasion resistant coating is bonded, such as by epoxy material 26, to the inner face of support end 16. The element 12 is encapsulated with epoxy material 29. All of the foregoing is conventional in the art.

In accordance with the invention, any suitable material can be used for the support such as, for example, stainless steel, MONEL, HASTALLOY-C/B, aluminum, titanium, CPVC plastic, PVC plastic, KYNAR, TEFLON, Carpenter-20, etc.

As shown if FIG. 1, energy from element 12, when excited, is transmitted through the thickness t of the support end 16 to the interface with the gap 22. If there is no acoustic energy transmitting material such as a liquid in the gap, that is, the gap is dry, the energy is attenuated and little or none of it reaches the inner face of the other support end 18. If a liquid is present in the gap 22, that is, the gap is wet, the energy from the element travels across the gap 22, is reflected from the inner face of the other support end 18 back to and through the support end 16 to the element 12 which now acts as a receiving element.

A portion 33 of the acoustic energy emitted from element 12 that travels through the support end 16 is reflected back to the element 12 by the interface of the two different materials of support end 16 and the gap 22. This interface is either support end material-air or support end material-liquid. This energy portion 33 is reflected in either case of the gap 22 being wet or dry. In effect, the energy portion 33 is usable to measure the thickness of the support end 16 between the bonded face of element 12 and the support end-gap interface. If the element 12 becomes dis-bonded from the inner face of support end 16, that is, it becomes separated from the epoxy 26 or the epoxy dis-bonds from the inner face of support end 16, there will be no energy portion 33 transmitted to the support end-gap interface and no energy reflected back to element 12 from this interface. Also, there is no main energy signal available to be transmitted across gap 22. If there is a partial dis-bonding, there either will be no reflected signal or it will be significantly different from a normal reflected signal. Accordingly, the energy portion 33 is usable as a self-test signal for measuring the integrity of the element bonding. The self-test is valid in both conditions of the gap being wet or dry.

FIG. 1A shows another embodiment of sensor similar to that of FIG. 1 in which two elements 12 and 12a are used. Here the Second element 12a is mounted in a manner similar to the first element 12, as described with respect to FIG. 1, to the second end 18 of the sensor support structure. Connecting wires (not shown) pass through and are embedded in the support stem 20 for connection to the electrodes on the element 12a. In FIG. 1A, element 12 is used as a transmitter and element 12a as a receiver. That is, the main energy from transmitter element 12 is not reflected from the inner face of opposing support end 18 but is instead received by the element 12a on support end 12a. The functions of elements 12 and 12a can be interchanged.

In FIG. 1A, the receiver element 12a is subject to the same type of dis-bonding problems described above as element 12. As described below, the present invention also provides a dis-bonding self-test for both elements 12 and 12a of a two element type sensor by alternately using each element in a transmitting mode.

FIG. 2 shows a sensor 40 of the non-contacting type. Here, the body 42 is of any suitable plastic material, as well as metal or glass, and is attached to a vessel or pipe 50 by a strap or other suitable fastener (not shown). Here, the single element 12 is bonded by a suitable material 13, such as an epoxy as described above, to the inner face of the wall of the sensor body 42. There is usually an energy coupling material, such as petroleum jelly or similar material, between sensor body 42 and the wall of the vessel to which it is mounted. That is, the vessel wall is effectively part of the sensor body.

The acoustic energy transmitted by the element 12 passes through the wall of the vessel 50 to which the sensor 40 is attached into and across the interior of the vessel toward the opposing interior wall of the vessel. When there is liquid in the vessel at a level where the sensor is located the acoustic energy reaches the vessel opposing wall from which it is reflected back to the element 12. Reception of the reflected energy signifies that liquid is present in the vessel. If there is no liquid in the vessel at the level where the sensor 40 is located, then the acoustic energy is dissipated as it travels across the interior of the vessel and no signal is reflected from the opposing wall back to the sensor. In this sensor there is a reflection of part of the transmitted energy from the interface between the interior wall of the vessel to which the body is mounted and the vessel interior, whether wet or dry. This reflected energy can be used for a dis-bonding self-test as described above.

With respect to the sensors of FIG. 1 and 1A, the following relations exist:

(1) for a one element sensor (FIG. 1);

$T_r=2l/2V_L$ and (2) for a two element sensor (FIG. 1A);

$T_d=1/V_L$

For both types of sensors the arrival time of the original transmitted pulse is:

$T_r=2t/V_m$ where, t is the wall thickness of the support on which the element is mounted, l is the distance between the signal transmitting element and the reflector (or second) receiving element, $V_L$ is the velocity of the acoustic energy in the material (liquid) in the gap 22, $V_m$ is the velocity of the energy in the support structure, $T_s$ is the arrival time in a single element sensor, $T_d$ is the arrival time in a dual element sensor, and $T_r$ is the arrival time in the wall thickness of the support structure.

The same relationships apply for the non-contacting sensor of FIG. 2 as for the single element sensor of FIG. 1. Here, the inner face of the vessel 50 directly adjacent to the sensor corresponds to the face of the gap end 16 of the sensor of FIG. 1 to which the element 12 is mounted. The inner face of the vessel across its diameter from the sensor corresponds to the other end gap 18 of the sensor of FIG. 1.

Figure 4:
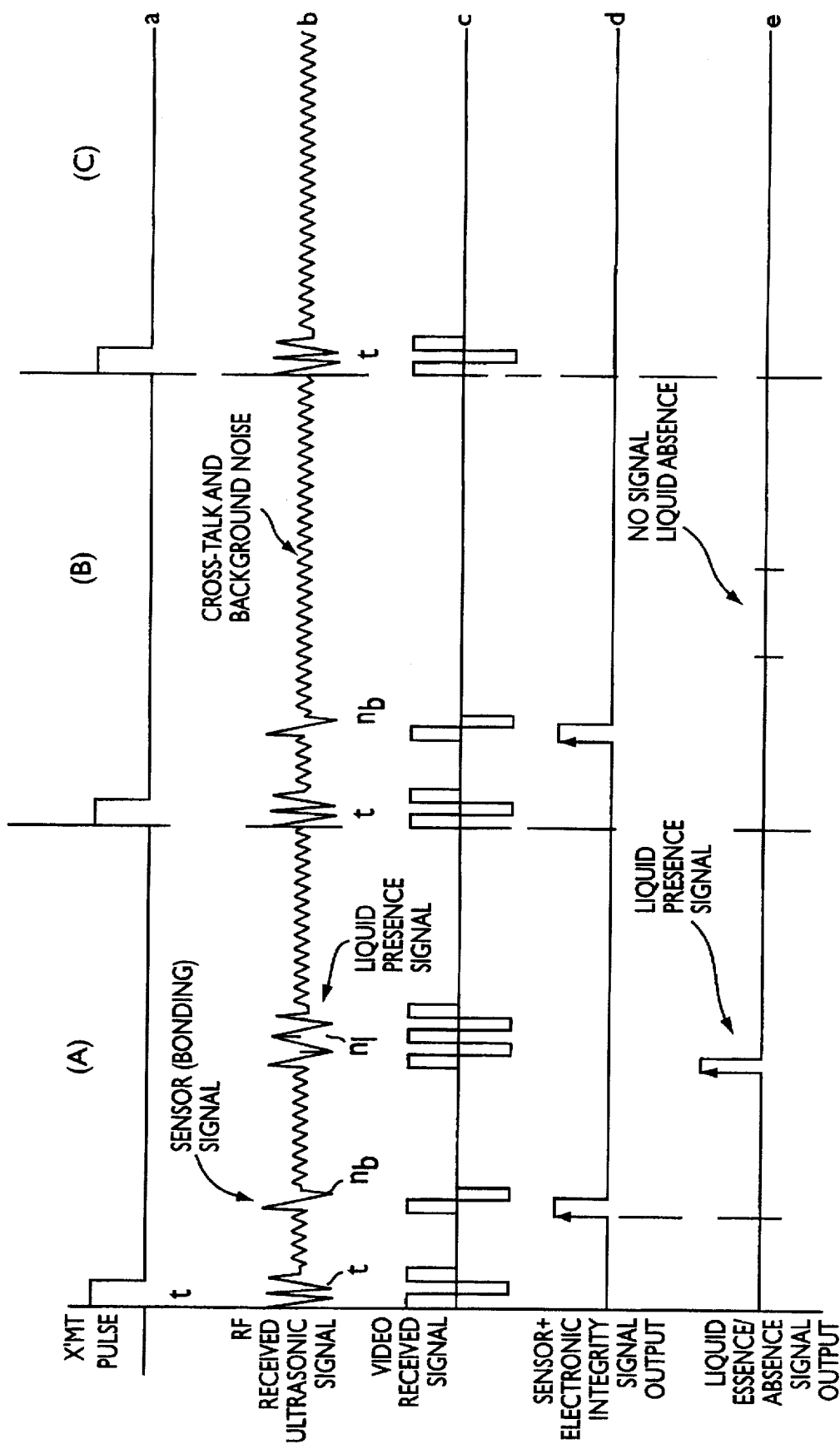
FIG. 4 is a timing diagram related to the circuit of FIG. 3.

FIGS. 3 and 4 show an embodiment of the invention that utilizes a mapping technique to check the integrity of the bonding of the sensor element(s) on a self-test basis. FIG. 3 is a circuit diagram of the electronic components and FIG. 4 shows the signal timing diagram. FIG. 4 is divided across its width into three sections illustrating three different conditions, these being:

(A) piezoelectric element bond OK and liquid in the sensor gap or interior of the vessel, (B) element bond OK and no liquid in the sensor gap or vessel interior, and (C) element dis-bonded, whether or not there is liquid in the sensor gap or vessel interior.

The system of FIG. 3 includes, as shown in the upper left corner of the drawing, the single element sensor 10 of FIG. 1, with the element 12 bonded to the wall of the part 16 of the support forming the gap, or the non-contacting sensor 40 of FIG. 2. A programmable microprocessor 70 receives its supply voltage from a suitable source (not shown) through a resistor 71. Microprocessor 70 controls a pulser 72 that repetitively produces a pulse, or burst of pulses, at timed intervals as controlled by the microprocessor. This pulse, t as shown in FIG. 4, is supplied to the sensor element 12 for transmission across the sensor gap, as shown on line a of FIG. 4. With element 12 properly bonded to the wall of the sensor support, the signal from pulser 72 is transmitted through the support wall for the element and into the gap or vessel interior in which liquid may or may not be present.

After the signal is transmitted by element 12 the microprocessor then sets the circuit to be in the receive mode. The circuit remains in the receive mode until the microprocessor later controls production of the next pulse from the pulser 72 for transmission. With the circuit of FIG. 3 in the receive mode, the transmitted signals from the element 12 that are received upon reflection from the element 12 support surface-air or support surface-liquid interface are applied to an RF amplifier 76, preferably of a high gain type. If liquid is also present in the gap 22 (FIG. 1) or interior of vessel 50 (FIG. 2), a signal is also received back at element 12 after the transmitted signal is reflected from the opposing support surface (18 in FIG. 1 forming the gap or opposing wall of the vessel (FIG. 2) and applied to RF amplifier 76. The signal amplified by RF amplifier 76 is applied to the input of a high pass filter 80.

The received reflected signals are shown on line b of FIG. 4. In section (A), where the sensor is fully operative, that is, the element 12 is properly bonded to the sensor, and there is liquid in the sensor gap 22, a signal $r_b$ is reflected from the air-wall interface of the support end 16 to which the element 12 is bonded and a signal $r_L$ reflected from the opposing surface of support end 18. The signal $r_b$ reflected from the air-wall interface of support end 16 to which the element is bonded is received first. This is the signal used to check the sensor element 12 bonding integrity. If there is liquid in the sensor gap, the reflected signal $r_L$ indicating presence of the liquid is also received. The same two signals are received in the case of the non-contacting sensor 40 of FIG. 2.

Under all of the conditions illustrated in the three sections (A), (B) and (C) of FIG. 4, there is noise, or cross-talk, present. This is shown by the jagged indication line along the timing diagram line b baseline. This is caused, at least in part, by signal leakage from the back and sides of element 12. The leakage signal is reflected back to element 12 from parts of the sensor support structure while the circuit is in the receive mode. The cross-talk also should be discriminated against to prevent false indications of either proper element bonding or liquid presence.

The output of the filter 80 is applied to a high speed analog/digital (A/D) converter 84, for example of type PNA 7509 made by Philips Corporation. A suitable digital signal processing (DSP) circuit also can be used. The filter 80 output can be applied directly to the A/D converter 84 or alternatively it can be applied through an envelope detector 82 which can be used to smooth the received signal before application to the A/D converter 84. This smoothed signal is shown on line c of FIG. 4 and retains the amplitude characteristic of the received signals on line b. If desired, a type of microprocessor can be used that incorporates an on board A/D converter.

In a typical application the microprocessor 70 can have an internal clock operating at 10 MHz and the signal produced by pulser 72 to be transmitted by the sensor is illustratively in the range from 100 KHz to 3 MHz. With the 10 MHz microprocessor clock frequency, the cycle time, or sampling frequency, allotted for transmission of the signal and its reception can illustratively be 100 nanoseconds. Assuming, for example, that the sensor operates to transmit a signal at 1 MHz, then the A/D converter sampling the received signal at a 10 MHz rate will take ten samples of each cycle of the sensor signal as received. That is, ten digital numbers will be produced for each cycle of the received signal.

The A/D converter 84 processes each RF or RF envelope signal it receives on an amplitude basis to produce a set, ten in the example being described, of digital numbers. Each of the numbers can be, for example, an eight bit digital word. Longer or shorter word lengths, sample rates and sample times can be used as desired in accordance with the types of microprocessor 70 and A/D converter 84 being used. In the example, one set of ten digital numbers is produced by A/D converter 84 in response to receipt of each one cycle of signal $r_b$. A second set of ten digital numbers is produced in response to each cycle of signal $r_L$ if there is liquid detected in the sensor gap or in the interior of vessel in the case of the non-contact sensor of FIG. 2. The two sets of digital numbers produced will be different since the received signal $r_L$ will have a different amplitude after travelling through the liquid than the leakage energy that produces signal $r_b$.

If element 12 of a sensor is dis-bonded, usually no digital numbers are produced since no energy is transmitted either to the interface or across the sensor gap or vessel interior. This condition is shown in section (C) of FIG. 4.

Microprocessor 70 has an internal memory in which a signature of valid received signals are stored. That is, considering the example of the 1 MHz transmitted signal energy and an A/D converter with a 10 MHz sampling rate, the microprocessor internal memory will have a table of ten numbers in time order sequence with digital values corresponding to signals that are received for each of the received reflected signals $r_b$ and $r_L$. The table for each of these two numbers is different. The tables are programmed into the microprocessor memory during manufacture of the sensor since all of the parameters are known, e.g. distance from the sensor element to the support surface and thickness of the support surface, distance of the gap or vessel interior, etc.

Each digital word received from the A/D convertor, whose numerical value corresponds to a sample of the received signal, is stored in the microprocessor memory. The set of stored numbers for each cycle of a received signal $r_L$ and $r_b$ constitutes a signature for the received signal.

Each set of numbers corresponding to a cycle of a received signal is compared with the stored signature number set, or table, of numbers corresponding to a valid signal. The comparison is done by a conventional statistical cross-correlation technique that is performed by microprocessor 70. The comparison gives a decision as to whether or not the received signal is valid, that is, the element is not dis-bonded.

Both the time of receipt of signal $r_b$ relative to the start of a cycle by transmission of signal t and the set of amplitude representative digital numbers corresponding to $r_b$ should always be substantially the same since the distance between the element 12 and the support end wall-gap interface is fixed. The time of arrival of signal $r_L$ relative to the start of each cycle and its set of amplitude representative digital numbers may be different depending upon the type of liquid in the gap or vessel, viscosity, temperature, liquid turbulence and other factors. This corresponds to section (A) of FIG. 4. The cross-correlation program can be designed to accommodate for this by, for example, producing a valid signal decision if the set of numbers is within a certain range of the sets of numbers in the tables. For example, a change in the temperature and/or viscosity of the liquid causes a change in the time $T_s$ and/or amplitude of the received signal $r_L$. The former can be taken care of in the microprocessor by shifting the set of A/D produced numbers relative to the stored table of numbers corresponding to a valid signature. Amplitude variations of the received signal can be taken care of by giving the cross-correlation program an error range.

Alternatively, the cross-correlation program can be set to recognize different types and characteristics of liquids based upon the set of numbers produced by the signal $r_L$. For example, there can be a look-up table corresponding to different liquids and/or the characteristics relating thereto or the microprocessor can utilize a calculation formula.

If the element 12 is properly bonded and there is no liquid in the sensor gap, there is a received signal $r_b$ but there is no received signal $r_L$. Therefore only one set of digital numbers is produced corresponding to $r_b$. This corresponds to section (B) of FIG. 4. If the element 12 is dis-bonded, neither signal $r_b$ or $r_L$ will be produced. This is true whether or not there is liquid present in the sensor gap. Consequently, neither set of digital numbers is produced for this situation which corresponds to section (C) of FIG. 4. If there is leakage energy from a partially dis-bonded element that results in production of a signal $r_b$ that is not valid, a different set of digital numbers will be produced than in the case of the signal $r_b$ produced for a sensor with a properly bonded element. A set of incorrect numbers detected during processing is indicative of sensor malfunction and can be indicated by a distinctive alarm signal.

After the sets of digital numbers produced by the A/D converter are cross-correlation processed by the microprocessor 70, the microprocessor produces an output that is applied to an output module 85. The output module produces an indication signal that corresponds to the element 12 dis-bonding self-test, if $r_b$ was produced and received, and liquid presence, if signal $r_L$ was produced and received. If an element is dis-bonded neither of the signals $r_b$ or $r_L$ will be produced. This condition can be indicated, for example, by an alarm signal. The output module 85 signals can be of standard 4 ma/20 ma (yes/no) current level or RS 232 serial output as is conventional in the control process art.

The transmit and receive modes of the sensor electronics are continuously produced on a repetitive cycle basis under control of microprocessor 70. After the end of the receive mode portion of each cycle, there can be a short rest time for processing of the information received by the microprocessor and production of the signal or signal corresponding to the state of the sensor element bonding (self-test).

A switch 69 is connected to a port of the microprocessor 70 to set the self-test to either demand or continuous mode. A remotely locate switch can be used to actuate the self-test on demand. In an on demand configuration the microprocessor can be programmed to process the rb signal for a few cycles and then return to normal operation.

The circuit of FIG. 3 can be used with a two element sensor Such as shown in FIG. 1A. Such a sensor is shown in the lower left part of FIG. 3. As explained above, in such a sensor one element 12 usually serves as the transmitter and the other element 12a as the receiver. To be able to check both elements for dis-bonding, a mode switch 102 is provided. Switch 102 is shown in mechanical analog form but can be implemented by an electronic switching circuit. Here, the microprocessor 70 is programmed to control mode switch 102 to switch the functions of elements 12 and 12a from transmitting to receiving and the circuit connections from the pulser 72 to the RF amplifier 76. When this is done, each element alternately serves as a transmitter and is checked in the manner described above. Here, however, the signal $r_L$ is produced upon receipt of the transmitted signal by the element across the gap which is connected as a receiver element.

Figure 5:
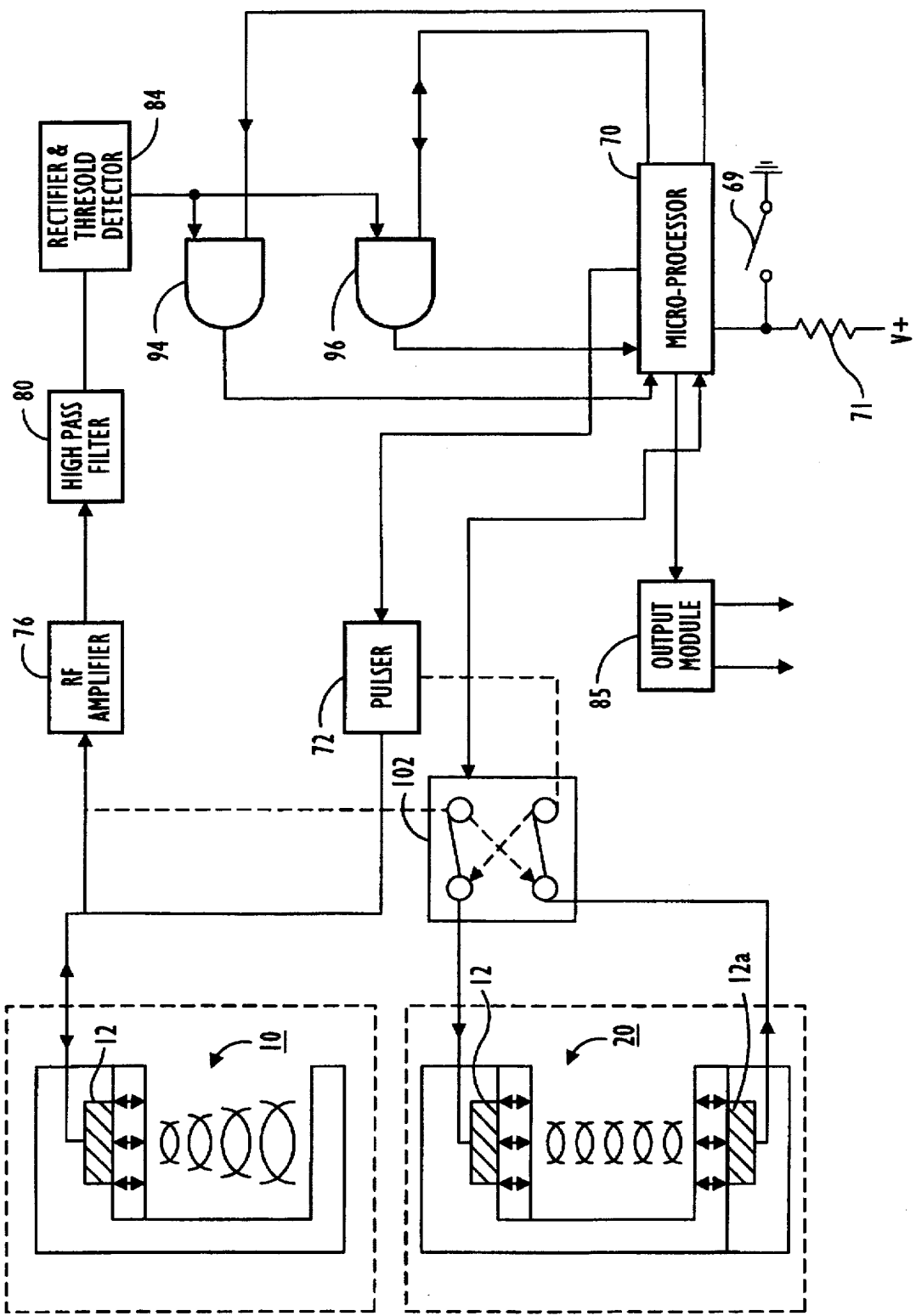
FIG. 5 is a schematic block diagram of another embodiment of a circuit with continuous or demand self-test capability.
Figure 6:
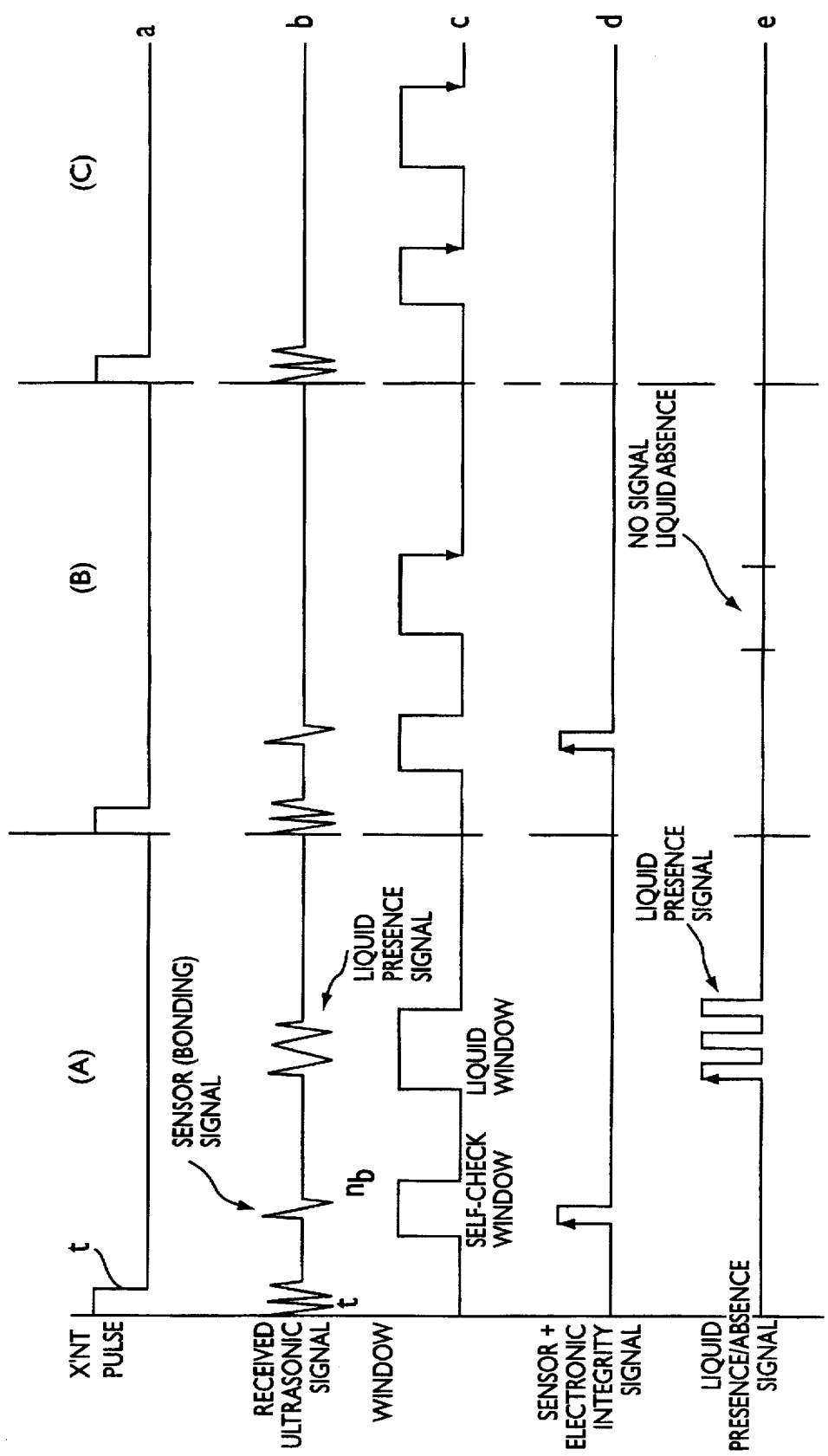
FIG. 6 is a timing diagram related to the circuit of FIG. 5.

Another embodiment of the invention is shown in FIGS. 5 and 6 where the same reference numerals have been used for the same components as in FIGS. 3 and 4. This embodiment is explained considering the single element sensor of FIG. 1. Here, the microprocessor 70 controls the pulser 72 to send the single narrow or burst of transmit pulses to the sensor element 12 for transmission through the epoxy bonding material 26 and the support structure end 16 into the gap 22. If the gap is wet, the energy travels across the gap and is reflected from the inner face of the other sensor end 18 back to element. Assuming that element 12 is properly bonded to the support, a portion of the energy from the transmitted pulse will also be reflected from the interface of the support end 16 and the gap back to element 12. The signals received by element 12 pass through the RF amplifier 76, high pass filter 80 and threshold detector 84.

Microprocessor 70 is programmed to produce two gating time windows, as shown in FIG. 6 line c, one for the self-check signal and the other for the main liquid detection signal. These gating window signals, which can be logic 1 signals, are applied to one input of each of respective logic AND gates 94 and 96. The time of the windows is calculated based upon the thickness of the support structure end part to the end part being measured by the self-test signal and the sensor gap across which the main signal used to sense liquid presence travels. The other input to each of gates 94 and 96 is the signal output from a threshold detector 84. The output of each gate circuit is applied to a respective control input of microprocessor 70. If a signal is received at the element 12 during the time of a respective window, it passes through a respective gate 94, 96 to cause the microprocessor to produce a signal applied to the output module 85.

FIG. 6 is a timing diagram illustrating the operation of the circuit of FIG. 5. FIG. 6 is divided into the same three sections (A), (B) and (C) as in. FIG. 4. In FIG. 6, line a shows the transmitted pulse, line b the reflected signals received by the element 12 and line c the windows generated by the microprocessor and used for the gates 94 and 96. The self-test window will always precede the liquid presence window since the time $t_d$ (reflection from end support-air or liquid interface) is always less than $t_s$ (round trip travel time in a one element sensor with liquid in the gap).

In section (A), element 12 is properly bonded and there is liquid in the gap, the self-test signal reflected from support portion 16 is received during the occurrence of the self-test window, as shown in line d, and the liquid presence signal is received during the time of the liquid presence window, as shown on line e. The microprocessor output to the output module produces a sensor check output, as shown on line f, and a liquid presence control output, as shown on line g.

In section (B) of FIG. 6, no liquid in the gap but the element bond is satisfactory. Here there is still a reflection of energy from the support-gap interface so that a signal is produced during the time of the self-test window as shown on line d. In this case the output module 85 produces only a valid self-test signal, i.e. that the sensor is functioning properly.

In section (C) of FIG. 6, where the element is dis-bonded from the support, no energy is transmitted by the element through the support structure into the gap. Therefore, no signal is received during the time of either of the self-test and liquid presence windows. This result occurs whether or not there is liquid present in the gap.

The circuit of FIG. 5 also can be used to check disbonding of both elements of a two element sensor through the use of the mode switch 102. Here, the time $t_d$ (travel time of energy across gap through liquid in a two element sensor) is greater than the time $t_d$ (reflection from element used as the transmitter to end support-air or liquid interface).

We claim:

1. An ultrasonic sensor comprising:
    a support structure having a wall;
    an element for transmitting and receiving ultrasonic energy bonded by an adhesive to one face of said wall, the other face of said wall having an interface with a fluid medium;
    a transmitter for periodically supplying energy to said element to be transmitted through said wall to said interface, a portion of the energy periodically supplied to said element being transmitted through said adhesive to said wall and reflected back through said adhesive to said element when said element is properly bonded by said adhesive to said one face of said wall; and
    a receiver coupled to said element to detect reception of energy reflected back to said element through said adhesive during at least a part of the time when said element is not transmitting energy.

2. An ultrasonic sensor as in claim 1 wherein said receiver selectively receives the energy signal reflected back to said element at a predetermined time corresponding to the distance of the surface of the element bonded to said wall and said interface.

3. An ultrasonic transducer as in claim 2 wherein said receiver produces a time window at a time corresponding to said predetermined time, and an indicator for producing a signal corresponding to a received energy signal occurring at the time of the window.

4. An ultrasonic sensor as in claim 1 wherein said receiver further comprises a memory for storing a signature corresponding to reception of the energy reflected back to said element to correspond to said element being properly bonded to said one face of said wall, and means for comparing the received reflected signal with the received reflected signal.

5. An ultrasonic sensor comprising:
    a support structure having a wall;

an element for transmitting and receiving ultrasonic energy bonded by an adhesive to one face of said wall, the other face of said wall having an interface with a fluid medium;

a transmitter for periodically supplying energy to said element to be transmitted through said wall to said interface; and a receiver coupled to said element to detect reception of energy reflected from said interface back to said element during at least a part of the time when said element is not transmitting energy, wherein said receiver includes a memory for storing a digital signature corresponding to reception of energy reflected from said interface to correspond to the element being properly bonded to said one face of said wall and a converter for converting the signal of the energy received by the element to a digital number.

6. An ultrasonic sensor as in claim 5 wherein said converter comprises an analog-to-digital converter responsive to the amplitude of the received energy signal to produce the digital number.

7. An ultrasonic sensor as in claim 6 wherein said receiver further comprises means for comparing the digital number corresponding to the amplitude of the received energy signal with the stored signature digital number and to produce an indication of correspondence or lack of correspondence.

8. An ultrasonic sensor as in claim 6 wherein said analog-to-digital converter sequentially samples the received energy signal to produce a series of digital numbers.

9. An ultrasonic sensor as in claim 8 wherein said receiver includes a microprocessor for comparing the series of digital numbers with said signature digital number by a cross-correlation technique.

10. An ultrasonic sensor as in claim 8 wherein said receiver includes a memory for storing on a time sequential basis the series of digital numbers and a microprocessor for comparing the series of digital numbers with said signature digital number and for producing an indication of correspondence or lack of correspondence therebetween.

11. An ultrasonic sensor as in claim 5 wherein said digital signature represents information relative to the amplitude and time of reception of the received energy signal with the element being properly bonded to said wall.

12. An ultrasonic sensor for sensing the presence of a liquid in an area comprising:

a support structure having an interface with a fluid medium;

at least one element for transmitting and receiving ultrasonic energy bonded to said support structure;

a transmitter for periodically supplying energy to said at least one element to be transmitted through said wall to said medium wherein a portion of the energy periodically supplied to said at least one element being transmitted through the bond to said support structure and reflected back through the bond to said at least one element when said at least one element is properly bonded to said support structure; and a receiver coupled to said at least one element to detect reception of energy transmitted through a liquid medium during at least a part of the time when said at least one element is not transmitting energy, said receiver including a memory for storing a digital signature corresponding to characteristics of the liquid through which the energy is transmitted, a converter for converting the signal of the energy received by the element to a digital number and for comparing the digital number with the stored digital signature.

13. An ultrasonic sensor as in claim 12 wherein said support structure has a pair of opposing walls with a gap therebetween, said at least one element being bonded to at least one of said walls with the energy being transmitted through the gap having the medium to the opposite wall.

14. An ultrasonic sensor as in claim 13 wherein said at least one element is bonded to each said wall, one such element for transmitting energy and the other said element for receiving energy transmitted through the medium.

15. An ultrasonic sensor as in claim 12 wherein said memory of said receiver includes information corresponding to at least one of temperature and viscosity of the fluid medium for comparison with the digital number corresponding to the received signal.

16. An ultrasonic sensor comprising:

a support structure having a wall;

an element for transmitting and receiving ultrasonic energy bonded by an adhesive to one face of said wall, the other face of said wall having an interface with a fluid medium;

a transmitter for periodically supplying energy to said element to be transmitted through said wall to said interface, a portion of the energy periodically supplied to said element being transmitted through said adhesive to said wall and reflected back through said adhesive to said element when said element is properly bonded by said adhesive to said one face of said wall;

a receiver coupled to said element to detect reception of energy reflected from said interface back to said element during at least a part of the time when said element is not transmitting energy and to detect reception of energy transmitted through a liquid medium during at least another part of the time when said element is not transmitting energy, said receiver including a memory for storing a digital signature corresponding to characteristics of the liquid through which the energy is transmitted and a digital signature corresponding to reception of energy reflected from said interface to correspond to the element being properly bonded to said one face of said wall; and a converter for converting the signal of the energy received by the element to a digital number and for comparing the digital number with the stored digital signatures.

* * * * *